United States Patent
Rönnberg et al.

(10) Patent No.: US 10,675,189 B2
(45) Date of Patent: Jun. 9, 2020

(54) ABSORBENT PRODUCT COMPRISING FOAM MATERIAL

(71) Applicant: ESSITY HYGIENE AND HEALTH AKTIEBOLAG, Göteborg (SE)

(72) Inventors: Peter Rönnberg, Göteborg (SE); Philip Blomström, Göteborg (SE)

(73) Assignee: ESSITY HYGIENE AND HEALTH AKTIEBOLAG, Göteborg (SE)

(*) Notice: Subject to any disclaimer, the term of this patent is extended or adjusted under 35 U.S.C. 154(b) by 0 days.

(21) Appl. No.: 16/466,455

(22) PCT Filed: Dec. 5, 2016

(86) PCT No.: PCT/SE2016/051213
§ 371 (c)(1),
(2) Date: Jun. 4, 2019

(87) PCT Pub. No.: WO2018/106156
PCT Pub. Date: Jun. 14, 2018

(65) Prior Publication Data
US 2019/0350768 A1   Nov. 21, 2019

(51) Int. Cl.
*A61F 13/472* (2006.01)
*A61F 13/537* (2006.01)
(Continued)

(52) U.S. Cl.
CPC ...... *A61F 13/472* (2013.01); *A61F 13/15723* (2013.01); *A61F 13/475* (2013.01);
(Continued)

(58) Field of Classification Search
CPC .... A61F 13/53747; A61F 2013/530861; A61F 13/53713; A61F 2013/530802–530854; A61F 13/47
See application file for complete search history.

(56) References Cited

U.S. PATENT DOCUMENTS

| | | | | |
|---|---|---|---|---|
| 4,389,211 A | * | 6/1983 | Lenaghan | A61F 13/15203 604/383 |
| 5,397,316 A | * | 3/1995 | LaVon | A61F 13/535 604/369 |

(Continued)

FOREIGN PATENT DOCUMENTS

| CN | 102006847 A | 4/2011 |
|---|---|---|
| CN | 105101926 A | 11/2015 |

(Continued)

OTHER PUBLICATIONS

First Chinese Office Action dated Nov. 5, 2019 issued in Chinese patent application No. 201680091299.3 (6 pages) and its English-language translation thereof (7 pages).

(Continued)

*Primary Examiner* — Susan S Su
(74) *Attorney, Agent, or Firm* — Faegre Drinker Biddle & Reath LLP

(57) ABSTRACT

An absorbent product includes a liquid permeable topsheet, a liquid impermeable backsheet, and an absorbent core enclosed between the topsheet and the backsheet. The absorbent core includes an absorbent fibrous layer, a liquid inlet foam layer, and a carrier layer, in which a transversally central region is arranged in the liquid inlet foam layer. The transversally central region extends along the entire longitudinal length of the absorbent core and includes a plurality of slits arranged in a pattern, wherein the slits are dilated slit openings in a part of the central region within an intermediate portion of the absorbent core, and the slits are non-dilated slits in parts of said central region within one or both of front and rear portions of the absorbent core.

18 Claims, 5 Drawing Sheets

(51) Int. Cl.
  *A61F 13/15* (2006.01)
  *A61F 13/475* (2006.01)
  *A61F 13/512* (2006.01)
  *A61F 13/53* (2006.01)

(52) U.S. Cl.
  CPC ........ *A61F 13/5123* (2013.01); *A61F 13/537* (2013.01); *A61F 2013/530802* (2013.01)

(56) References Cited

U.S. PATENT DOCUMENTS

| | | | |
|---|---|---|---|
| 5,941,863 A | 8/1999 | Guidotti et al. | |
| 10,159,608 B2* | 12/2018 | Johansson | A61F 13/4751 |
| 2004/0230184 A1* | 11/2004 | Babusik | A61F 13/53713 |
| | | | 604/378 |
| 2008/0140042 A1* | 6/2008 | Mukai | A61F 13/49001 |
| | | | 604/385.23 |
| 2014/0295134 A1* | 10/2014 | Wood | B01J 20/28054 |
| | | | 428/135 |
| 2015/0148769 A1* | 5/2015 | Johansson | A61F 13/4751 |
| | | | 604/385.23 |
| 2015/0173971 A1* | 6/2015 | Johansson | A61F 13/4751 |
| | | | 604/385.101 |
| 2017/0027778 A1* | 2/2017 | Stridfeldt | A61F 13/53747 |
| 2018/0161218 A1* | 6/2018 | Jonegren | A61F 13/476 |
| 2018/0338869 A1* | 11/2018 | Jonegren | A61F 13/475 |
| 2019/0328588 A1* | 10/2019 | Saevecke | A61F 13/51104 |

FOREIGN PATENT DOCUMENTS

| | | |
|---|---|---|
| CN | 105828776 A | 8/2016 |
| RU | 2391080 C2 | 6/2010 |
| WO | WO-97/31601 A1 | 9/1997 |
| WO | WO-2009/105000 A1 | 8/2009 |
| WO | WO-2015/094068 A1 | 6/2015 |

OTHER PUBLICATIONS

Russian Decision to Grant dated Nov. 28, 2019 issued in Russian patent application No. 2019120844 (10 pages) and its English-language translation thereof (6 pages).

\* cited by examiner

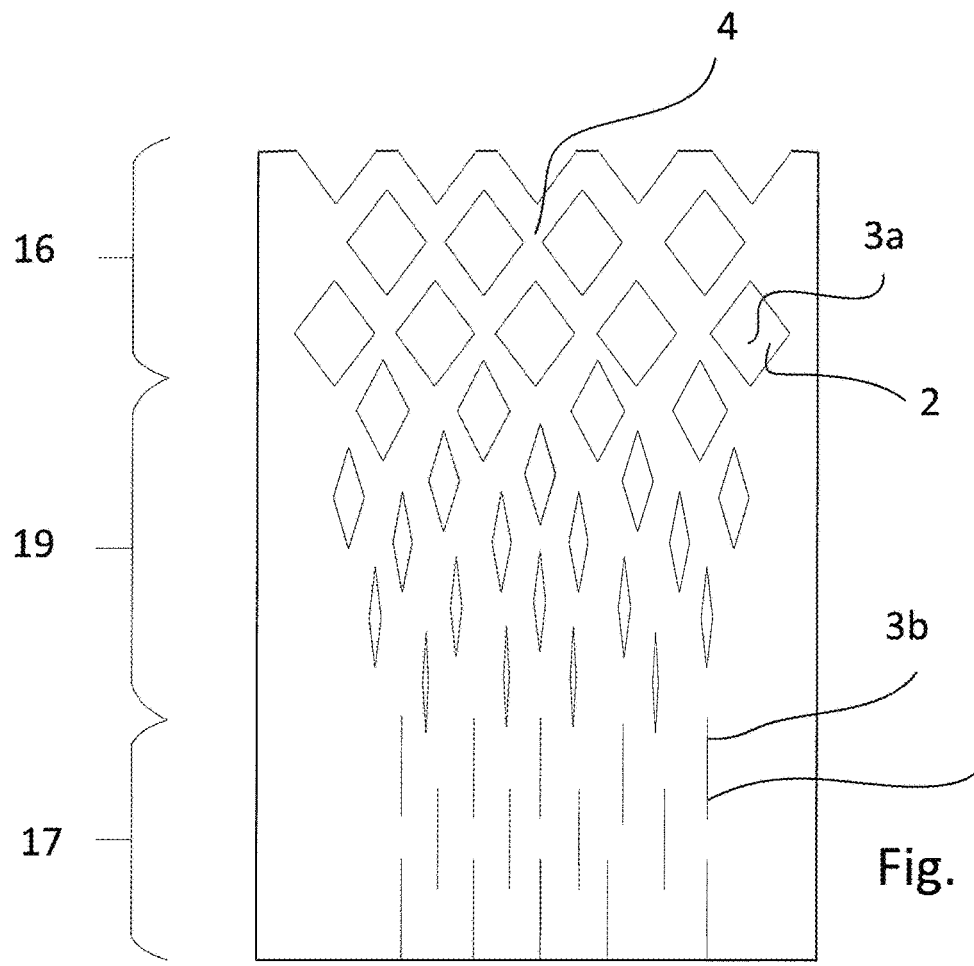
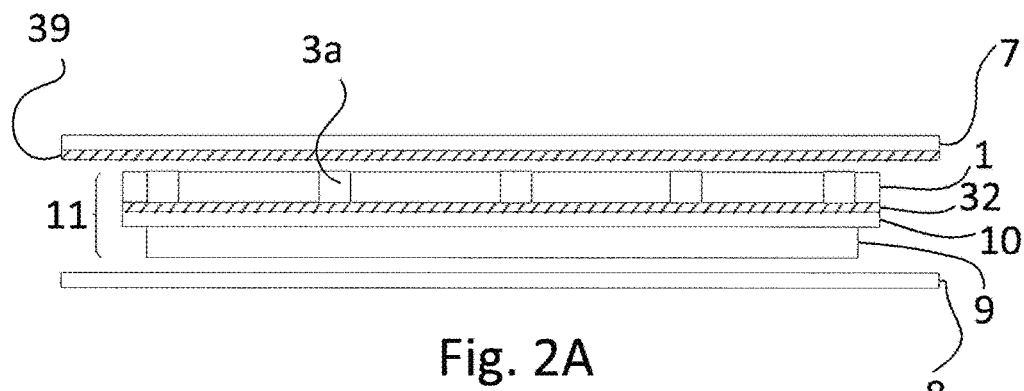
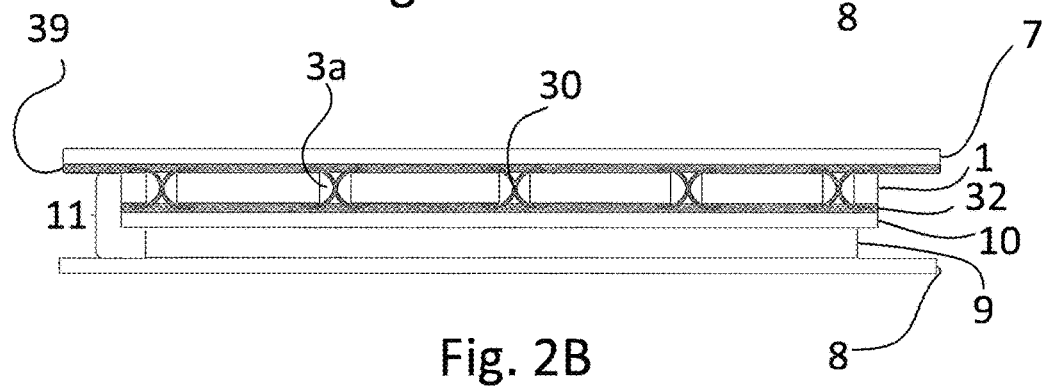

ABSORBENT PRODUCT COMPRISING FOAM MATERIAL

CROSS-REFERENCE TO RELATED APPLICATION

This application is a § 371 National Stage Application of PCT International Application No. PCT/SE2016/051213 filed on Dec. 5, 2016, which is incorporated herein in its entirety.

TECHNICAL FIELD

The present disclosure relates to an absorbent product, such as a sanitary napkin, including a liquid permeable topsheet, a liquid impermeable backsheet, and an absorbent core enclosed there between, and to a method for manufacturing such absorbent products.

BACKGROUND

For absorbent products such as sanitary napkins there are high requirements that they are discreet, soft and comfortable to wear and at the same time have a reliable security against leakage.

For sanitary napkins intended to absorb menstrual fluid being more viscous than urine, it is often more difficult for the body fluid to reach the absorbent core below the top sheet. Menstrual fluid may easily move around on the user facing side of the top sheet under the influence of gravity, motion and pressure by the user. Migration of menstrual fluid to the edges of the product increases the likelihood of leakage, and further smears the menstrual fluid against the skin of the user making cleanup more difficult. It is desirable that products used for absorbing menstrual fluids are able to give the user a feeling of secureness and a visual impression that the menstrual liquid is absorbed by an absorbent core. Further, it is desired to minimize the cost of manufacturing the absorbent products.

SUMMARY

The present disclosure relates to an absorbent product including a liquid permeable topsheet, a liquid impermeable backsheet, and an absorbent core enclosed between the topsheet and the backsheet. The absorbent core has a length extending in a longitudinal direction of the absorbent product, between a front edge and a rear edge, and has longitudinally extending side edges. The absorbent core includes an absorbent fibrous layer arranged on the side of the absorbent core, which is closest to the liquid impermeable backsheet, a liquid inlet foam layer arranged on the side of the absorbent core, which is closest to the liquid permeable topsheet, and a carrier layer arranged between the liquid inlet foam layer, and the absorbent fibrous layer. The absorbent core includes a front end portion, a rear end portion, and an intermediate portion located between the front and rear portions, in the longitudinal direction of the absorbent core. The absorbent core further includes a transversally central region arranged in the liquid inlet foam layer, said region extending along the entire longitudinal length of the absorbent core and having substantially longitudinally extending side edges. The central region includes a plurality of slits arranged in a pattern, which covers the central region. The slits are in the form of dilated slit openings in a part of the central region, which is located in the intermediate portion of the absorbent core, and the slits are in the form of non-dilated slits in parts of said central region, which are located in one or both of the front and rear portions, of the absorbent core.

The dilated slit openings in the intermediate portion of the liquid inlet foam layer may be formed from a plurality of slits, which have been dilated into dilated slit openings by transversally extending a web of liquid inlet foam material, from which the liquid inlet foam layer is made, before incorporation into the product. The non-dilated slits may have a maximum transversal opening width of 0-1 mm, and the dilated slit openings may have a maximum transversal opening width of 1.5-15 mm, or 1.5-5.0 mm. The front and/or rear end regions may include non-dilated slits, but no dilated slit openings.

The absorbent core may further include a front transition region located between the front end region and the intermediate region in the longitudinal direction of the absorbent core, and/or a rear transition region located between the rear end region and the intermediate region in the longitudinal direction of the absorbent core, wherein the slits gradually dilate in said front and/or rear transition regions, from non-dilated slits to dilated slit openings in a direction from said front and rear transition regions, toward the intermediate region. The front and rear end regions may each have a length in the longitudinal direction from the front end edge and the rear edge, respectively, of 5-50 mm, or 10-25 mm, or 15-20 mm.

The carrier layer may be made of a material, which has a different color than the liquid inlet foam material, from which the liquid inlet foam layer is made. Colored areas may be present on the carrier layer in the front and rear end regions, of the absorbent core, and the liquid inlet foam material may have an opacity of 20-100%. The liquid permeable topsheet may include a see-through material, through which the colored areas or different color of the material of the carrier layer in relation to the inlet foam material is visible.

The liquid inlet foam layer may include side edge regions, located on either side of the central region in the transversal direction of the absorbent product, between the central region and the longitudinal side edges, of the absorbent core, and wherein the liquid inlet foam material in each of said side edge regions is free from slits.

The central region may have a transversal width and the absorbent fibrous layer may have a minimum width, where the transversal width of the central region is equal to or smaller than the minimum width of the absorbent fibrous layer.

The present disclosure further relates to a method of manufacturing the above absorbent product, including the steps of cutting a plurality of slits in a central region of a continuous web of liquid inlet foam material, said slits extending longitudinally in the machine direction; extending the web of liquid inlet foam material transversally in the cross machine direction, whereby the slits are dilated into dilated slit openings; applying adhesive to a continuous web of carrier material; combining the continuous web of liquid inlet foam material and the web of carrier material into a combined web; cutting inlet foam layer components from the combined web; providing absorbent components; enclosing the inlet foam layer component and absorbent component between a continuous web of topsheet material and a continuous web of backsheet material; joining at least the topsheet material and the backsheet material along the outer edges of the absorbent product; cutting the combined material into a desired shape, thus obtaining the absorbent product, wherein: when extending the web of liquid inlet foam material transversally in the cross machine direction, the width of said web of liquid inlet foam material is extended to a predetermined desired transversal width; and when applying adhesive to the continuous web of carrier material, the adhesive is applied intermittently, so that adhesive is applied on sections of the web of carrier material, which correspond to the intermediate portion of the absorbent core, and sections, which correspond to the front and rear end portions, of the absorbent core are free from adhesive; or wherein when extending the web of liquid inlet foam material transversally in the cross machine direction, the width of said web of liquid inlet foam material is extended intermittently, so that sections of the web of liquid inlet foam material is extended to a predetermined desired transversal width, and sections, which correspond to the front and rear end portions, of the absorbent core retain their original unextended width; and when applying adhesive to the continuous web of carrier material, the adhesive is applied continuously to the web of carrier material.

The slits cut in the web of liquid inlet foam material may have a length in the longitudinal direction is 3.0-20.0 mm, or 4.0-16.0 mm, or 5.0-12.0 mm.

The method may further includes the step of applying adhesive to the surface of the web of topsheet material facing the liquid inlet foam component before enclosing the core components, and pressing the layers together so that the topsheet material layer is attached to the carrier layer through the dilated slit openings formed in the liquid inlet foam layer.

In the method, the web of carrier material may have a different color than the web of liquid inlet foam material, or it may include one or more colored areas applied thereto. The one or more colored areas may be printed on a body facing surface or on a garment facing surface of the web of carrier material.

BRIEF DESCRIPTION OF THE DRAWINGS

FIG. 1B shows a detail of the product shown in FIG. 1A.

FIG. 2A shows a schematic cross-sectional view of the product of FIG. 1 across the line A-A in FIG. 1.

FIG. 2B shows in a schematic cross-sectional view schematically how the topsheet and the carrier layer are attached to each other through the openings in the liquid inlet layer along the line A-A in FIG. 1.

DETAILED DESCRIPTION OF PARTICULAR EMBODIMENTS

Figure 1A:
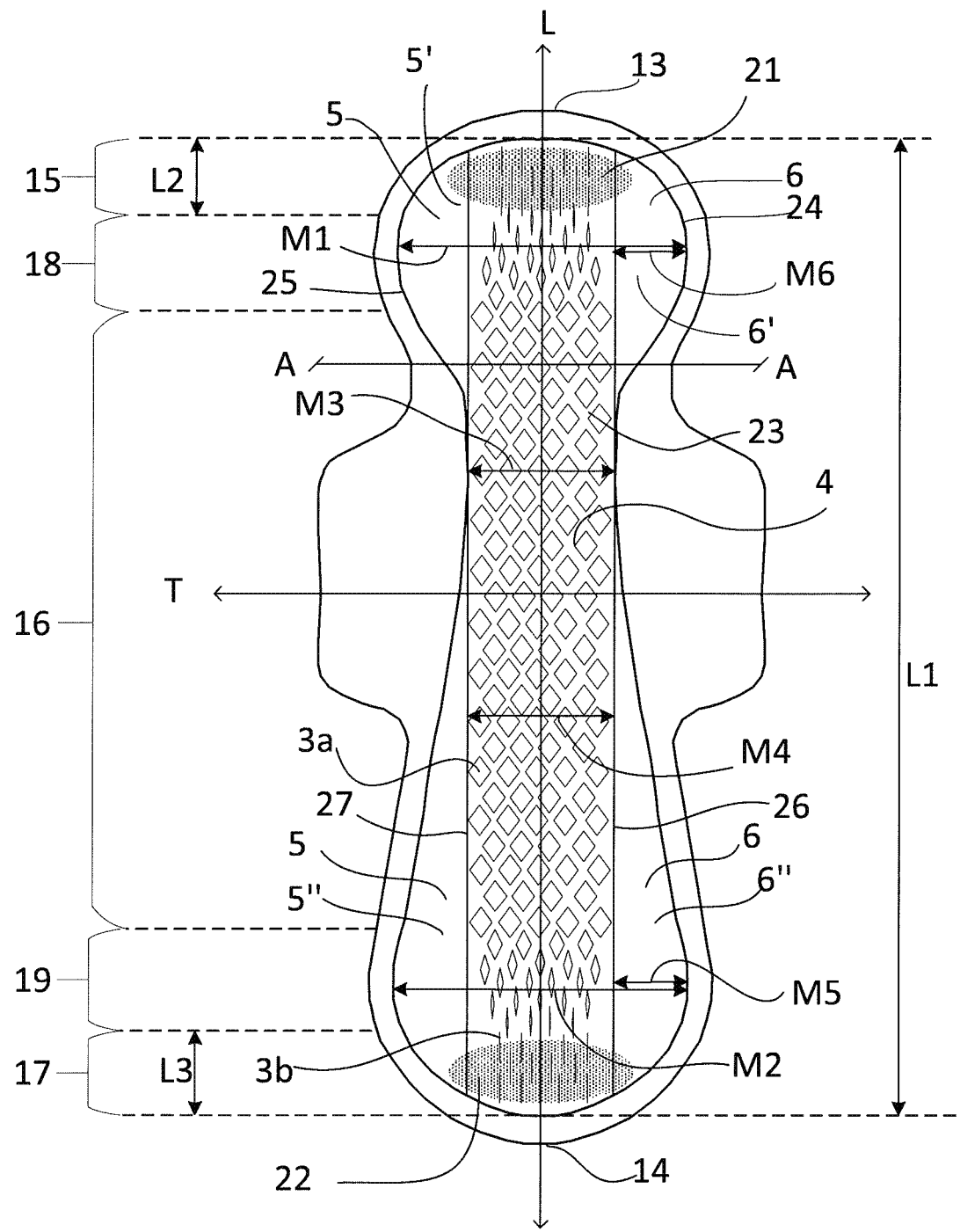
FIG. 1A shows a schematic top view of an absorbent product according to the present disclosure.

The present disclosure relates to a hygiene absorbent product, such as a sanitary napkin, a panty liner, an incontinence shield, or a diaper. The absorbent product includes an absorbent core disposed between a liquid permeable topsheet and a liquid impermeable backsheet. The absorbent product has a transversal rear end edge intended to be orientated rearwards during use of the absorbent article, and a front end edge intended to be facing forwards towards the abdomen of the wearer. The absorbent core includes an absorbent fibrous layer arranged on the side of the absorbent core, which is closest to the liquid impermeable backsheet, and a liquid inlet foam layer arranged on the side of the absorbent core, which is closest to the liquid permeable topsheet, and a carrier layer arranged between the liquid inlet foam layer and the absorbent fibrous layer. An absorbent product including a foam material is experienced as soft and is also aesthetically pleasing for many users. The continuous structure of many foam materials gives good pliability and an ability to spring back and to substantially return to its original form after having been exposed to outer loading, which contributes to the wearer comfort. The absorbent core extends in a longitudinal direction between a front edge and a rear edge, and has substantially longitudinally extending side edges, and includes a front end portion, a rear end portion, and an intermediate portion located between the front and rear portions in the longitudinal direction of the absorbent core.

The absorbent core includes a transversally central region, which extends in the longitudinal direction of the absorbent core and has substantially longitudinally extending side edges. The central region provided in the liquid inlet foam layer may be located substantially parallel to a longitudinal center line in the longitudinal direction of the absorbent product, and need not follow the outer contour of the absorbent core or the absorbent product, and it may have substantially the same width over its entire length. The liquid inlet foam layer will typically cover the entire absorbent fibrous layer. In the transversally central region, the liquid inlet foam layer is provided with a plurality of slits arranged in a pattern, such that the pattern covers the area of the liquid inlet region. In a part of the central region, which is located in the intermediate portion of the absorbent core, the slits are in the form of dilated slit openings, whereas in parts of said central region, which are located in one or both of the front and rear portions of the absorbent core, the slits are in the form of non-dilated slits. The part of the central region, in which the slits are in the form of dilated slit openings, will have the function of a liquid inlet region, and the location in the intermediate portion of the absorbent core corresponds to the crotch region of the product, and thus may be located, during use, in a position where a liquid insult is most likely. The parts of the central region, in which the slits are in the form of non-dilated slits, will have the function of a barrier region which can contribute to prevent leakage at the front and/or rear end of the absorbent product. When the front and/or rear end regions include non-dilated slits, but no dilated slit openings, the leakage protection is substantially the same as if the foam material were entirely free from openings in this region. The foam as such typically does not absorb liquid to any substantial extent.

The plurality of inlet openings in the liquid inlet foam layer may be formed from a plurality of longitudinally extending slits, which have been dilated into openings by transversally extending a web of liquid inlet foam material from which the liquid inlet foam layer is made, before incorporation into the product, or may be obtained by punching/perforating. Forming the plurality of slits by slitting and extending the inlet foam material has the advantage that no material is cut out from the web, which saves money due to less waste of material, and also improves the handling in the production process by avoiding having a lot of small pieces cut out from the material that may contaminate both the process equipment and the final product.

In order to obtain a central region in the liquid inlet foam layer, which has dilated slit openings in some areas and non-dilated slit openings in other areas, by slitting and extending, the web of liquid inlet foam material can be extended to a greater extent in portions which are to include dilated slit openings, than in portions which are to include non-dilated slit openings, and be subsequently secured to an adjacent component in the product to hold the foam layer in place, Alternatively, the web of liquid inlet foam material can be extended to the same extent along the whole length, and be secured intermittently to an adjacent component in the product, so that the liquid inlet foam layer is not secured in portions which are to include non-dilated slit openings, and the foam material will thus relax and return to a non-extended condition.

The central region may typically extend along the entire longitudinal length of the liquid inlet foam layer, which facilitates manufacture of the foam layer from a continuous web of foam material, from which the inlet foam layer is subsequently cut, since a continuous pattern of cut slits can be provided in a transversally central region of the continuous web of foam material, which means that leakage barrier regions can be obtained in the resulting absorbent product, although the slit pattern has been provided continuously.

The front and rear end regions may each have a length in the longitudinal direction of the absorbent product from the front end edge, and the rear edge, respectively, of 5-50 mm, or 10-25 mm, or 15-20 mm. The length of the end regions is chosen depending on the desired characteristics of the absorbent product, such as the size of the product, the intended use, and desired size of the liquid inlet area. A length above 5 mm allows effective manufacture, and a length below 50 mm allows the presence of a liquid inlet region between the front and rear end regions.

The central region may further include transition regions located between the one or both end region and the intermediate region in the longitudinal direction of the absorbent core, in which the slits gradually dilate from non-dilated slits to dilated slit openings in a direction from the respective end region toward the intermediate region. Thus a front transition region is located between the front end region and the intermediate region, a rear transition region is located between the rear end region and the intermediate region in the longitudinal direction of the absorbent core. The provision of transition regions further facilitates manufacture of the absorbent product, since the extension of the foam material in order to dilate the slits into slit openings can then be performed or maintained only along parts of the length of the foam material where fully dilated openings are desired, and other parts can remain non-extended or non-secured.

Due to the lateral extension of the material, the openings formed by slitting and extending the inlet foam material will be widest at their longitudinal center. When the slit is cut as a straight line in the longitudinal direction of the product, the opening will have a diamond shape. The openings can also have other shapes, which can be obtained by cutting slits having a curved shape, e.g. forms as a wave. The non-dilated slits may have a maximum transversal opening width of 0-1 mm, in order to obtain a leakage barrier in the areas where the slits are non-dilated. The dilated slit openings may have a maximum transversal opening width of 1.5-15 mm, or 1.5-5.0 mm, in order to obtain effective liquid inlet in the liquid receiving area.

The longitudinal slit length may be 3.0-20.0 mm, 4.0-15.0 mm or 5.0-12.0 mm. For sanitary napkins intended to absorb menstrual fluid being more viscous than urine, it is often more difficult for the body fluid to reach the absorbent core than for absorbent products intended for urine. Menstrual fluid may easily move around on the user facing side of the top sheet under the influence of gravity, motion and pressure by the user. Migration of menstrual fluid to the edges of the product increases the likelihood of leakage, and further smears the menstrual fluid against the skin of the user making cleanup more difficult. By having a slit length of 5-12 mm, menstrual fluid will reach the absorbent core more easily. The longitudinal length of the dilated openings may differ from the slit length, due to the transversal extension of the foam material, which can decrease the longitudinal length somewhat as the slit are formed into dilated openings. The dilated inlet slit openings may have a width in a transversal direction of the absorbent core which is 30-100% of their length in the longitudinal direction of the absorbent core, in order to be large enough to effectively let through liquid into the absorbent layer.

The dilated slit openings may have a longer dimension in the longitudinal direction of the absorbent product than in the transversal direction, thus giving the slit opening a generally oval shape in the longitudinal direction, which gives the user a visual impression of good liquid wicking in the longitudinal direction. The plurality of slit openings creates a pattern of the openings in the liquid inlet material. The slits may be provided in staggered rows extending in the longitudinal direction, where the slits in each longitudinal row of slits have a longitudinal length, and are located at a slit distance between adjacent end points of two sequential slits in the row, and the longitudinal rows are staggered such that adjacent rows are offset by 50% in the longitudinal direction, with a row distance between two adjacent rows. The distance between adjacent inlet openings in liquid inlet region may be 1.0 to 9.0 mm. A short distance between the openings improves the inlet rate. The liquid inlet foam material may alternatively have other slit patterns, or combinations of different slit pattern. Such slit patterns of the openings may be formed by providing slits with different lengths, or by having slits with different slit distances between the slits. Also, irregular patterns may be used. The total open area formed by the slit openings in the horizontal plane of the liquid inlet foam material in the central region may be 30-80% of the total area in the horizontal plane of the liquid inlet foam material in the central region, in order to efficiently let liquid through and at the same time provide sufficient stability.

The liquid inlet foam layer may further include side edge regions located on either side of the central region in the transversal direction of the absorbent product, between the central region and the longitudinal side edges of the absorbent core. In these side edge regions, the liquid inlet foam material is free from slits. As the foam typically does not absorb liquid to any substantial extent, these side edge regions can function as leakage barriers, and can also provide softening of the edges of the absorbent core. The side edge regions have a smooth surface against the user's skin, due to the absence of openings in the foam. Each side edge region of the front and rear portions may have a maximum transversal width of 5.0-50.0 mm, 20-50 mm, or 5.0-20.0 mm.

The absorbent core may have straight and substantially parallel longitudinal side edges. Alternatively, the absorbent core may be curved so as to attain a shape by means of which it includes a front part and a rear part, and an intermediate part, where the transversal width of the intermediate part is smaller than the transversal width of the front and rear parts, thus giving the absorbent core an hourglass shape. By providing an intermediate portion having a narrower width than the front and rear portions, the configuration of the absorbent core, and of the absorbent product, can be better adapted to anatomy of the user's body. The crotch part is a portion which is intended to be placed against the crotch of a wearer during use of the product and to constitute the main acquisition area for body fluid that reaches the absorbent product. The outer contour of the absorbent fibrous layer and the liquid inlet foam layer need not be the same, thus an hour-glass shaped absorbent fibrous layer can be combined with a liquid inlet foam having straight parallel longitudinal side edges. The width and length of the absorbent core referred to in this disclosure are the dimensions of the combined layers of the core, unless otherwise indicated.

In the part of the central region which functions as a liquid inlet region, i.e. where the slits in the liquid foam layer are dilated slit openings, the central region may have a maximum transversal width, which is equal to or smaller than the minimum width of the absorbent fibrous layer. The liquid inlet region is thus typically not wider than the absorbent core, thus ensuring that any portion of the liquid inlet region is located where a part of the fibrous absorbent layer is present. If the transversal width of the central region is smaller than the minimum width of the absorbent fibrous layer side edge regions are formed along the entire longitudinal length on each side of the absorbent core.

A transversal width of the liquid inlet region which is equal to the minimum transversal width of the absorbent core means that the liquid inlet region covers as much of the area as possible in the transversal direction, and if the absorbent core has an hourglass shape, no side edges are formed at the location of the minimum transversal width of the absorbent core. This minimizes the amount of inlet foam material needed for manufacture of the absorbent product, since the material from which the liquid inlet foam layer is made is extended until the liquid inlet region has the same width as the absorbent fibrous layer in its narrowest portion. In this case, front and rear side edge regions, which are free from slits, are formed transversally outside of the central region, in the front and rear part of the absorbent core.

The liquid inlet foam material may be hydrophobic or hydrophilic. Hydrophobic foam materials give hydrophobic edge regions, which can function as liquid barriers and will decrease the risk for edge leakage. The plurality of openings present in the central liquid inlet region ensures that the liquid reaches the absorbent layer of the core below the liquid inlet foam layer, even though the foam material is in itself hydrophobic. Also, hydrophobic foam material close to the user's skin can be beneficial from a skin care view, since a hydrophobic and dry surface may decrease the risk for bacterial growth and skin irritations.

The foam material may have an open cell structure or a closed cell structure. Foam materials used as liquid inlet layer in absorbent products are often open cell foams, so that liquid can easily enter the foam and consequently also the absorbent core below. However, due to the presence of the plurality of openings in the liquid inlet region, also closed cell foams can be used. In closed cell foams, the liquid will not so easily enter the foam structure itself, and therefore the foam material as such will be kept in a more dry condition, as compared to an open cell foam material, where the pores are connected with each other. The average pore size of the liquid inlet foam material may be greater than the average pore size of the absorbent fibrous layer arranged below the foam, resulting in a pore size gradient and a capillary suction force in the direction from the foam material towards the absorbent fibrous layer below the liquid inlet foam material.

The foam's pliability and flexibility reduces the risk of scrapes. Liquid inlet layers of air laid, cellulose-based layers and liquid inlet layers of non-woven material do not have the same ability to reduce the negative effect of the stiff edges that a stiff cellulose-based absorption layer causes. Flexible foam materials may spring back and return to substantially their original shape after having been exposed to outer loading, and are also pliable. Flexible foam materials also have a padding effect such that the foam material lines the stiff edges and creates a soft distancing element between the user's skin and the stiff edges of the absorbent fibrous layer. The softness and flexibility of a foam material may be of use for example in a premature baby diaper.

Examples of usable foams are polyolefin based foam, polystyrene based foam, PVC foam, polyvinyl alcohol foam, acrylate foam, polyurethane foam, epoxy foam, latex foam, urea-formaldehyde foam, melamine-formaldehyde foam, silicone foam, viscose foam, carboxymethyl cellulose (CMC) foam, starch form, chitosan foam, alginate foam, polyactide foam, polyglycolide foam and polycaprolactone foam.

The liquid inlet foam layer may be held in place by adhesive attachment to any adjacent component, for example the absorbent fibrous layer or the topsheet.

The liquid inlet foam layer material may be laminated to the carrier layer material in its extended condition so that the foam material is fixed to the carrier material with openings in their extended condition. In particular embodiments, the carrier layer has the seam surface extension as the foam layer. The absorbent product can include an adhesive layer arranged between the liquid inlet foam layer and the carrier layer, which covers at least an area corresponding to the liquid inlet region, and suitably covers the entire area of the carrier layer, to ensure that the openings within the liquid inlet region are held in a desired position. A suitable construction adhesive is "Adhesive Hotmelt", for example, from Henkel Adhesives, H B Fuller or Bostik. A suitable elastic adhesive is Dispomelt 723U from Henkel Adhesives.

The opacity of foam materials used for the liquid inlet layer can be influenced by a number of factors. Properties such as porosity, basis weight, density, and thickness affect the opacity due to scattering and absorption of light in the material. Also, the composition of a foam material can affect the opacity, and the presence of light absorbing/reflecting materials such as pigments or dyes. In particular embodiments, pigments are not included in a liquid inlet foam material, or added only in a small amount. Foam materials having various degrees of opacity are commercially available.

The carrier layer is liquid permeable and can be made of a nonwoven material, such as airlaid or meltblown or spunbond synthetic fibre nonwoven material, or tissue material, e.g. including cellulose fibres, or combinations thereof.

The absorbent product may also include an additional adhesive layer arranged between the liquid inlet foam layer and the topsheet, and wherein the topsheet is attached to the carrier layer through the liquid inlet openings in the liquid inlet region. Thereby, the liquid inlet foam layer will be held from two sides, which allows the open area of the liquid inlet region to be larger, so that the slitted foam material can be extended to a greater degree, which in turn leads to saving foam material. The liquid inlet foam material and/or the carrier material may be colored, such that the carrier layer arranged between the inlet foam layer and the absorbent fibrous layer may be made of a material, which has a different color than the liquid inlet foam material, from which the liquid inlet foam layer is made, whereby the difference between regions with dilated slit openings and with dilated slits can be visually emphasized. Furthermore, if the absorbent core includes an absorbent layer having a shape with a less extension than the foam, a colored layer between the liquid inlet foam layer and the absorbent layer can make the outer contour of the absorbent layer less easy to recognize by the user. A colored carrier layer below the liquid inlet foam layer visualizes the openings more clearly, so that they will be more easily recognized by the user. The color difference can be obtained by making the carrier layer and the liquid inlet foam layer from differently colored materials, or by applying colored areas in desired locations, e.g. by printing. The colored areas may present on the carrier layer in the front and/or rear end regions of the absorbent core, and thereby can function as a means of orienting the absorbent product correctly during use. The colored areas may be provided on the body facing side or the garment facing side of the absorbent product as long as they are visible from the body facing side of the absorbent core.

The liquid inlet foam material may have an opacity of 20-100%. It may be desired to allow colored areas located below inlet foam layer to be visible from the body facing side of the absorbent core, and the inlet foam layer may then be made of a material, having an opacity below 100%, for example 20-60%, so that it is sufficiently translucent and transparent for the colored area below the foam layer to be visible through the foam material layer. It is not necessary that the materials are fully transparent, instead it may be desired that color difference is somewhat obscured in order for the difference between the color seen through the dilated slit openings to be different from the color seen through the foam material. The color of the colored areas present on the carrier layer may be selected so that the colored areas are visible, or can at least be discerned, from the body facing side of the absorbent product. The liquid-permeable top sheet layer is arranged on a body facing surface of the product and is intended to be in contact with the wearer's skin during use. As said above, in particular embodiments, the liquid inlet foam material is free from added pigments, and thus has its original whitish color. This allows a wider range of colors to be used for the colored areas on the carrier layer, and improves the effect of the colored areas. The color hue and color density is selected taking the opacity of the liquid inlet layer material and the topsheet material into consideration, in order to obtain the desired visual impression in the absorbent product. The one or more colored areas located in the carrier layer may have different colors or different color intensity, in relation to each other in order to emphasize and visualize certain functions in the product.

Alternatively, the inlet foam layer may be made of a foam material having high opacity, i.e. close to 100%, for example 70-100%, so that a colored area below the foam material will not be visible through the foam material layer, unless openings are provided in it, and the colored area can thus function to indicate that the slits are non-dilated, and thus form a leakage barrier.

For example, the colored areas on the carrier layer may be green or blue in parts which become wet during use, e.g. the liquid receiving region, and may have pink or red tones in portions located at the front or rear end of the product to denote the front or rear part of the product. The colored areas on the topsheet may have the same colors as the colored areas on the carrier layer but with a different intensity, or may be different. For example purple areas or lines can be used to illustrate barriers. By selecting different colors and/or color intensities, function areas such as liquid inlet area and absorption zone, and front, rear and side barriers can be visualized. Indications to as to how to position the product during use can be provided for example by a colored area having a certain shape, e.g. a heart shape.

The colors of the colored areas provided on the carrier layer and the topsheet can be expressed in accordance with the CIELAB Color Scale, which is a color space specified by the International Commission on Illumination. It describes all the colors visible to the human eye and was created to serve as a device-independent model to be used as a reference (cf. CIE Publication 15.2 (1986), Section 4.2).

The CIELAB color space is organized in a spherical form with the L* axis running from top to bottom and the a* and b* axis being placed in a horizontal plane. In general, CIE L* scale values are units of light reflectance measurement, and the higher the value is, the lighter the color is since a lighter colored material reflects more light. The L* scale contains 100 equal units of division, absolute black is at the bottom of the scale (L=0) and absolute white is at the top of the scale (L=100). Thus in measuring L* values of the materials used in the absorbent articles in the context of the present disclosure, the lower the L* scale value, the darker the material. The a* axis is the axis red/green (+a*=red, −a*=green), while b represents the axis yellow/blue (+b*=yellow, −b*=blue). The L*, a* and b* values can be measured using any suitable equipment, for example the colorimeter MINOLTA mode CR-300 instrument (available from the Minolta Company, Japan) which provides the coordinates L*, a*, b* and from which the 4E* value between two color points can be determined.

The L*a*b* values of the colored areas can be measured on the material taken in-situ on the carrier layer as such and/or in-situ on body facing side of the finished absorbent product.

Figure 6:
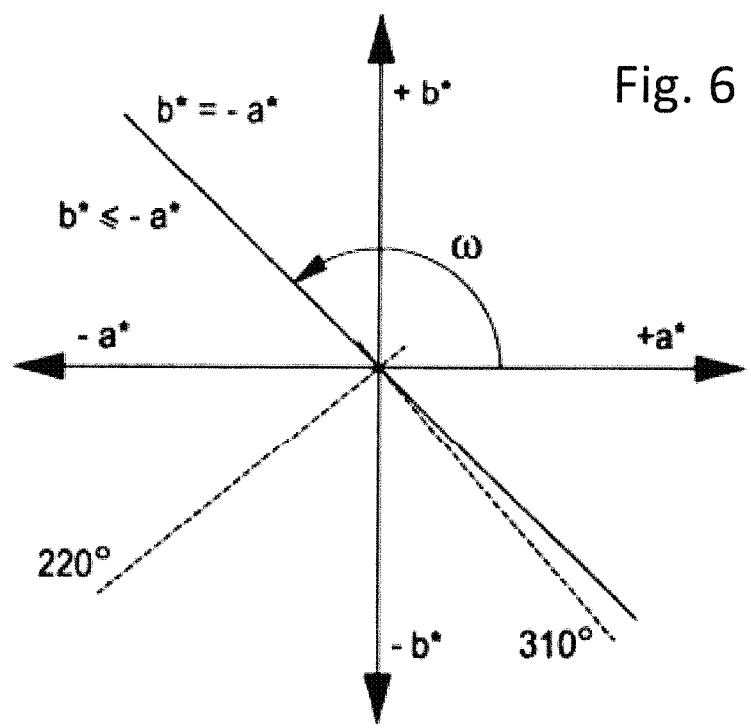
FIG. 6 shows the horizontal plane of the color sphere for L=50.

As said above, in particular embodiments, the hue of the color of the lateral zones is selected in the blue or green region rather than in the yellow or red region for aesthetic purpose. Furthermore it has been found that blue and green pigmented nonwoven may better be able to hide underlying stains of blood or urines. Thus the measured a* and b* values may be advantageously such that the relation b* less than or equal to −a* is fulfilled. This relation may also be expressed in term of angles values reported to the horizontal color disc represented on FIG. 6. Taking any color on the +a* axis as having an angle ω ("omega") of 0, any color on the +b* as having an angle ω of +90° and so forth, and in that case the relation b* less than or equal to −a* is equivalent to having an angle ω of from 135° to 315°. In certain embodiments, colors in the blue or lilac tone, for which an angle ω of from 135° to 315°, or 180°-290°, are used.

Opacity is measured according to International Standard ISO 2471:2008 (E)—Paper and board—Determination of opacity (paper backing)—Diffuse reflectance method. The method originates from the paper industry, but it is suitable also in this context. The measuring of the opacity includes the steps of carefully separating the inlet layer from the absorbent product; and measuring opacity on an area that is free from slits or apertures. In case the opacity varies over the area of the inlet layer (e.g. due to partial coloration or differences in basis weight, the least opaque area should be considered representative for the inlet layer. The opacity can be defined as: Opacity (%)=100×(1−intensity of the transmitted light/intensity of emitted light).

The topsheet layer and the backsheet layer of the absorbent product extend together laterally outside of the absorbent core along the whole circumference thereof. The liquid-permeable top sheet layer is arranged on a body facing surface of the product and is intended to be in contact with the wearer's skin during use.

The top sheet layer can include of any material liquid-permeable known for the purpose, i.e. soft and liquid pervious, such as a layer of nonwoven material or a perforated plastic film, plastic or textile mesh, and fluid permeable foam layers. The top sheet can also include a laminate of two or more sheets of the same or different topsheet material, or where the top sheet layer includes different materials, within different parts of the fluid permeable wearer-facing surface. In order for color differences or colored areas to be visible for the user, the liquid permeable topsheet may suitably include a see-through material, through which the colored areas or different color is visible. The combined topheet material and foam material may have a maximum opacity, which is sufficiently low for the color difference or colored areas to be visible through both these layers, for example an opacity of 20-70%. A see-through material can be a nonwoven or plastic material, which is sufficiently transparent for the color difference to be visible or at least perceived through the material; or it can be substantially opaque material including apertures through which the color difference is visible, such as an apertured plastic or nonwoven material. The see-through material may also be a textile mesh, having openings between the threads in the material, through which the color difference is visible.

The liquid-impermeable back sheet layer is arranged on a garment facing surface of the product and is intended to be in contact with the garments during use. Backsheet materials that are only fluid repellant may be used in instances where relatively small amounts of body fluid are expected to be taken up. The back sheet layer can include a liquid-impermeable plastic film, a nonwoven sheet which has been coated with a liquid barrier material in order to be fluid-impermeable, fluid impermeable foams and fluid impermeable laminates, or any other flexible material sheet which has the ability to withstand liquid penetration. However, it can be advantageous if the liquid-impermeable back sheet layer is breathable, i.e. permits the passage of water vapour through the back sheet. Furthermore, the backsheet may have an outer, garment-facing surface of a textile material such as nonwoven.

The absorbent fibrous layer can be made up of absorbent material, such as cellulose fluff pulp, tissue, etc. and may contain superabsorbents, i.e. polymer materials which are able to absorb body fluid corresponding to many times their own weight and form a hydrogel. The superabsorbents may be mixed with cellulose fluff pulp and/or may be arranged in pockets or layers in the absorbent fibrous layer. The fibres may be pulp fibres and the superabsorbent material may be polyacrylate-based particles.

Moreover, the absorbent core can further include non-absorbent components such as stiffening elements, shaping elements, binders, etc. The absorbent core may for example include absorbent material in the form of an embossed layer including cellulose pulp and superabsorbent particles. The absorbent fibrous layer may suitably have a density of 0.092-0.160 $g/cm^3$ and a basis weight 200-640 $g/m^2$. The absorbent core may further incorporate components for improving the properties of the absorbent core, such as binder fibers, fluid-dispersing materials, wetness indicators etc., as known in the art.

When the above absorbent product is in the form of a sanitary napkin, light incontinence guard or the like, it may further include fastening means for fastening of the absorbent product inside a supporting pant garment, such as a pair of underpants. The fastening means may be in the form of two longitudinally extending bands of pressure sensitive adhesive arranged on the garment-facing surface of the backsheet. The fastening means can be covered by a releasable protective layer, e.g. a siliconized paper, a nonwoven or any other releasable material as is known in the art. Before placing the absorbent product in the supporting pant garment, the protective layer is removed from the fastening means to expose the adhesive and make it available for fastening to the pant garment.

When manufacturing an absorbent product the same materials as described above in relation to the absorbent product can be used.

The above absorbent product can be manufactured by means of the following method. The method includes a step of cutting a plurality of slits in a central region of a continuous web of liquid inlet foam material, so that the slits extend longitudinally in the machine direction. The slits can be cut in a pattern, and have lengths and distances in relation to each other as described above in relation to the absorbent product. For example, the slits may have a length in the longitudinal direction of 3.0-20.0 mm, or 4.0-16.0 mm, or 5.0-12.0 mm. After having been slitted, the continuous web of liquid inlet foam material is extended transversally in the cross machine direction, whereby the slits are dilated into openings, having dimensions and patterns as described above in relation to the absorbent product. The extension can be done by grabbing the longitudinal side edges of the material and drawing them transversely away from each other. The web of liquid inlet foam material is extended transversally in the cross machine direction until the longitudinally central region has a desired transversal width, thereby dilating the slits into openings.

An adhesive is applied to a continuous web of carrier material, and the web of carrier material is combined with the continuous web of liquid inlet foam material into a combined web, which is subsequently cut into inlet foam layer components. The adhesive can be applied to the carrier material by spraying or application by means of slot nozzle equipment. Absorbent fibrous material is provided in the form of discrete absorbent fibrous components, which are combined with the inlet foam layer component and enclosed between a continuous web of topsheet material and a continuous web of backsheet material. At least the topsheet material and the backsheet material are joined along the outer edges of the absorbent product. The resulting combined material is cut into a desired shape, thus obtaining the absorbent product. The absorbent fibrous components can be obtained in any other suitable way, such as by cutting pieces of a desired shape from a continuous web of fibrous absorbent material, or by mat formation.

When extending the web of liquid inlet foam material transversally in the cross machine direction, the width of said web of liquid inlet foam material may be extended to a predetermined desired transversal width, and when applying adhesive to the continuous web of carrier material, the adhesive is then applied intermittently, so that adhesive is applied on sections of the web of carrier material, which correspond to the intermediate portion of the absorbent core, and sections, which correspond to the front and rear end portions of the absorbent core are free from adhesive.

Alternatively, when extending the web of liquid inlet foam material transversally in the cross machine direction, the width of said web of liquid inlet foam material may be extended intermittently, so that sections of the web of liquid inlet foam material is extended to a predetermined desired transversal width, and sections, which correspond to the front and rear end portions of the absorbent core retain their original unextended width, and when applying adhesive to the continuous web of carrier material, the adhesive is then applied continuously to the web of carrier material.

When the part of the central region of the absorbent product, which is intended to remain in extended condition is suitably secured in its extended state, to prevent the dilated openings from returning to a more closed condition. This can be done by means of adhesive attachment, wherein an adhesive is applied to parts of the area of the inlet foam layer itself or to adjacent components. The most effective attachment is obtained when substantially the entire surface that is in contact with an adjacent component is covered with adhesive, as a fine pattern or as a layer completely covering the surface.

In order to increase foam material saving, the web of liquid inlet foam material may be transversally extended until the longitudinally central region has a transversal width which is equal to the transversal minimum width of the absorbent core component.

The method may also include a step of applying adhesive to the surface of the web of topsheet material facing the liquid inlet foam component before enclosing the core components, and pressing the layers together so that the topsheet material layer attaches to the carrier layer through the dilated slit openings formed in the liquid inlet foam layer.

DESCRIPTION OF THE DRAWINGS

FIGS. 1-4 schematically illustrate the above described absorbent product and method by way of example.

FIG. 1A shows a top view of an absorbent product in the form of sanitary napkin having a longitudinal direction L and a transversal direction T, and FIG. 2A shows a cross section of the same product. FIG. 1B shows a detail of the liquid inlet foam layer of the product in FIG. 1A. The sanitary napkin of FIG. 1A is depicted with wings, which can as well be omitted. The absorbent product includes a liquid permeable topsheet 7, a liquid impermeable backsheet 8, and an absorbent core 11 enclosed between the topsheet 7 and the backsheet 8. The absorbent core 11 has a length L1 extending in a longitudinal direction of the absorbent product, between a front edge 13 and a rear edge 14 of the absorbent core, and it has substantially longitudinally extending side edges 24, 25. As can be seen in FIGS. 1A, 1B and 2, the topsheet 7 and backsheet 8 extend outside of the circumference of the absorbent core 11. In the shown example, the absorbent core 11 includes a front part having a front maximum transversal width M1, and a rear part having a rear maximum transversal width M2, and the absorbent core 11 further has an intermediate minimum transversal width M3 at a point located longitudinally between said front part and said rear part, where the absorbent core is narrower at the intermediate minimum transversal width M3 than at the front and rear maximum transversal widths M1, M2. The absorbent core 11 includes a front end portion 15, a rear end portion 17, and an intermediate portion 16, located between the front and rear portions 15, 17 in the longitudinal direction of the absorbent core 11. The front and rear end regions 15, 17 each have a length L2, L3 in the longitudinal direction L from the front end edge 13 and the rear edge 14.

As shown in FIGS. 1A and 1B, the liquid inlet foam layer 1 includes a plurality of slits 2 arranged in a pattern, which covers a transversally central region 4 provided in the liquid inlet foam layer 1 of the absorbent core 11. The central region 4 includes a liquid inlet area 23, located in the crotch region of the absorbent product, and barrier areas located at the front and rear portions 15, 17, and in the shown example also transition regions 18, 19 located between the barrier areas located at the front and rear portions 15, 17 and the liquid inlet area 23. The central region 4 includes a plurality of slits 2 arranged in a pattern, which covers the central region 4. In the part of the central region 4, which is located in the intermediate portion 16 of the absorbent core, the slits 2 are in the form of dilated slit openings 3a. The area covered with dilated slits forms a liquid inlet area 23. In parts of said central region 4, which are located in one or both of the front and rear portions 15, 17 of the absorbent core, the slits 2 are in the form of non-dilated slits 3b. The front and rear end portions 15, 17 include non-dilated slits 3b, but no dilated slit openings 3a.

In the shown example, the central region 4 also includes a front transition region 18 located between the front end portion 15 and the intermediate portion 16 in the longitudinal direction of the absorbent core 11, and a rear transition region 19 located between the rear end portion 17 and the intermediate portion 16 in the longitudinal direction of the absorbent core 11, and the slits 2 gradually dilate in said front and rear transition regions 18,19, from non-dilated slits 3b to dilated slit openings 3a in a direction from said front and rear transition regions 18,19 toward the intermediate portion 16.

The plurality of dilated slit openings 3a provided in the liquid inlet foam layer 1 can be formed from a plurality of slits, which have been dilated into openings by transversally extending a web of liquid inlet foam material, from which the liquid inlet foam layer 1 is made, before incorporation into the product. This is shown in more detail in FIGS. 3A and 3B.

Figure 3A:
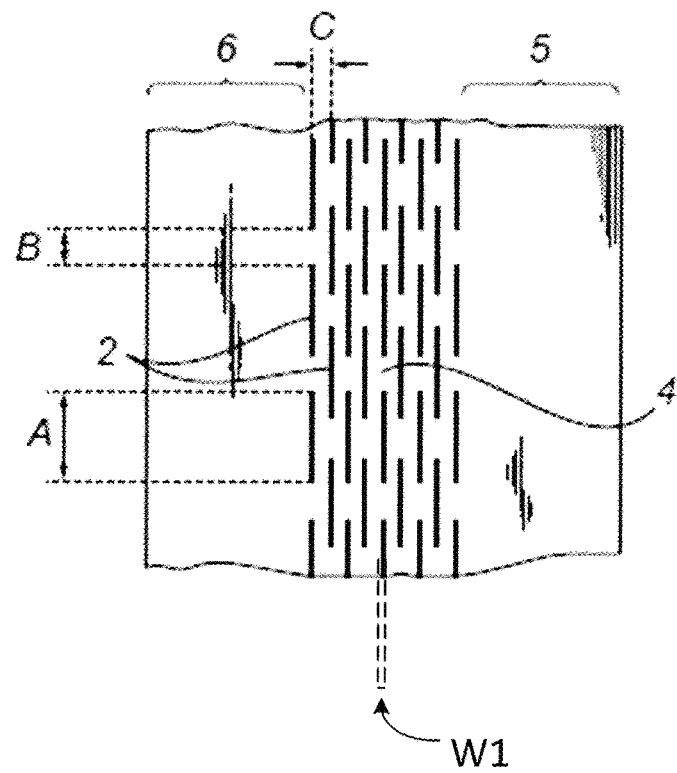
FIG. 3A shows a schematic top view of a liquid inlet foam material before it has been extended.

FIG. 3A shows a top view of a liquid inlet foam material 1 after it has been slitted but before it has been extended, and shows how a pattern of longitudinal slits 2 has been cut. The yet non-extended liquid inlet foam material 1 has in its transversal direction a central region 4 with slits and two side edge regions 5, 6 without slits. The slits 2 in FIG. 3A are straight, but may have any suitable shape such as for example wave-shaped. In the shown example, the slits 2 are provided in a pattern with staggered rows extending in the longitudinal direction of the inlet material 1. The slits 2 are located at a distance B within one longitudinal row, and adjacent rows are arranged at a distance C from each other in the transversal direction. Each slit 2 in the pattern has a slit length A. The non-dilated slits 3b have a maximum transversal opening width W1, and the dilated slit openings 3a have a maximum transversal opening width W2.

Figure 3B:
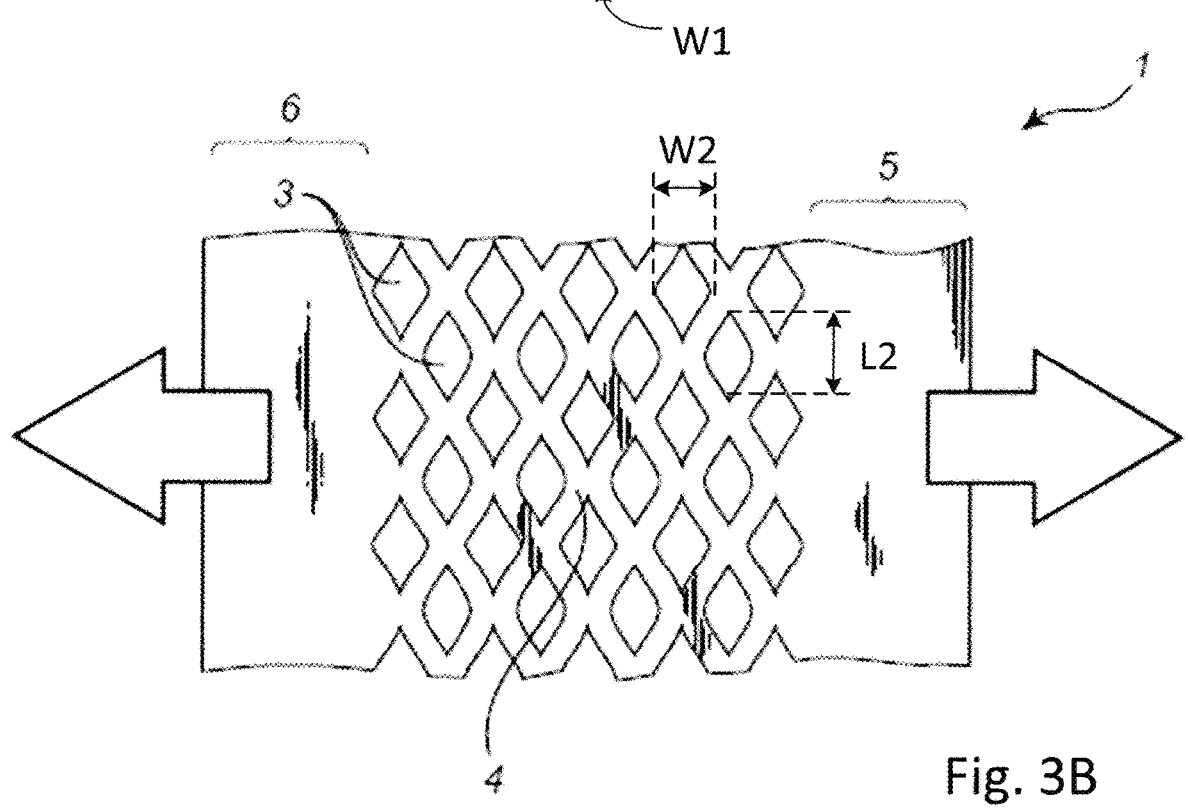
FIG. 3B shows a schematic top view of the liquid inlet foam material of FIG. 3A after it has been extended, i.e. after the slits have been dilated to form openings.

FIG. 3B the liquid inlet foam material of FIG. 3A after it has been extended in the direction transversal to the slit 2 direction, i.e. after the slits 2 have been opened to form openings 3. The slits 2 have now been dilated to diamond shaped slit openings 3a, or diamond pockets, and have a longitudinal length L2 and a transversal width W2. The side edge regions 5, 6 are still free from openings.

As seen best in FIG. 2A, the absorbent core 11 includes an absorbent fibrous layer 9 arranged on the side of the absorbent core, which is closest to the liquid impermeable backsheet 8, a liquid inlet foam layer 1 arranged on the side of the absorbent core, which is closest to the liquid permeable topsheet 7. FIG. 1A shows how the absorbent core 11 includes a transversally central region 4, which extends in the longitudinal direction of the absorbent core along the entire longitudinal length L1 of the absorbent core 11 and has substantially longitudinally extending side edges 26, 27, but the distance between these side edges can vary slightly. The absorbent product includes a carrier layer 10 arranged between the liquid inlet foam layer 1 and the absorbent fibrous layer 9, and an adhesive layer 32 is arranged between the liquid inlet foam layer 1 and the carrier layer 10. Further, an additional adhesive 39 layer can be arranged between the liquid inlet foam layer 1 and the topsheet 7, and the topsheet 7 can be attached to the carrier layer 10 through the dilated slit openings 3a by letting the adhesive layers 32, 39 join through the dilated slit openings 3a, which is illustrated in FIG. 2B at the point 30. When the layers of the absorbent product are combined, the carrier layer 10 will adhesively attach to the topsheet layer 7 through the openings 3 in the liquid inlet region 23, by means of the adhesive layers 39, 32.

Colored areas 21, 22 are present on the carrier layer 10 in the front and rear end regions 15, 17 of the absorbent core 11. A liquid inlet foam material 101 has an opacity of 20-60%, and suitably also a liquid permeable topsheet 7 in the form of a see-through material, through which the colored areas 21, 22 are visible.

In the shown example, the part of the central region 4 forming the liquid inlet region 23 has a transversal width M4, which is equal to the minimum transversal width M3 of the absorbent fibrous layer 9, so that side edge regions 5, 6 are arranged in the front and rear portions 15, 17 transversally outside of the liquid inlet region 23. In this example the side edges 16, 27 of the central liquid inlet region 23 are parallel to each other and to the longitudinal axis of the absorbent product, so that the width M4 is the same over its entire length. The side edge regions 5', 6' of the front portion 15 have a maximum width M6, and the side edge regions 5'', 6'' of the rear portion 17 have a maximum width M5. In the shown example, the width M6 of the front side edge regions 5', 6' is the same as the width M5 of the rear side edge regions 5'', 6'', but the front side edge region width M6 may also be smaller than the rear side edge region width M5.

The liquid inlet foam layer is free from liquid inlet openings in the side edge regions 5, 6. In the shown example, the transversal width M4 of the liquid inlet region 23 is equal to the minimum transversal width M3 of the absorbent core, which means that no side edge regions are present at this location. However, if desired side edge regions may be present transversally outside of the central portion along the entire length of the absorbent core.

Figure 4:
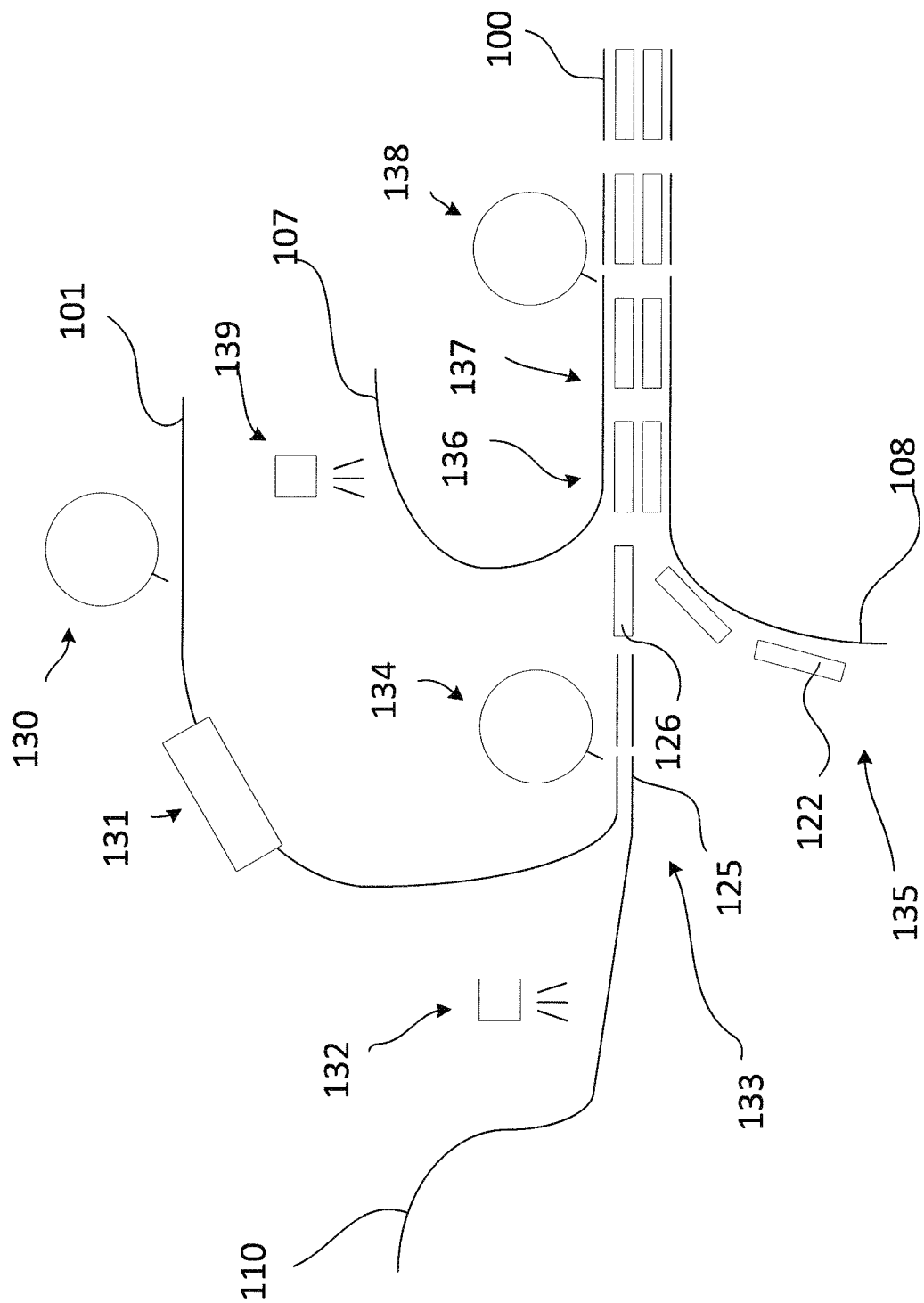
FIG. 4 shows schematically a method of manufacturing an absorbent product including an extended liquid inlet foam layer.
Figure 5:
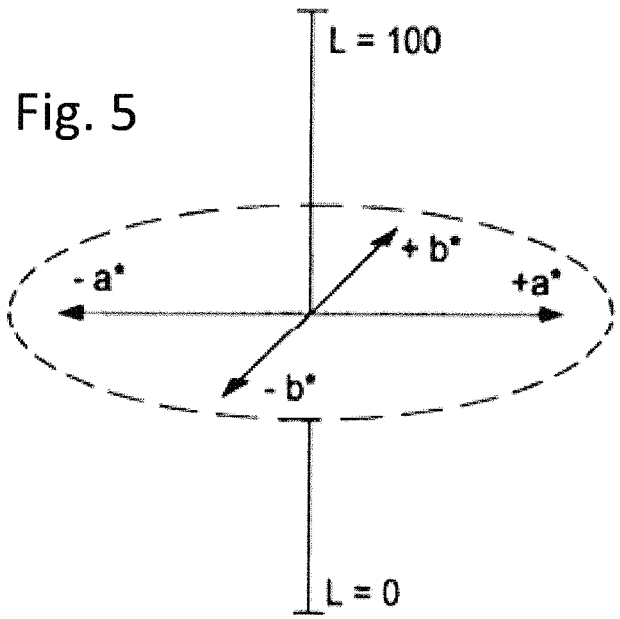
FIG. 5 shows the color "sphere" used for the representation of color in the CIELAB system.

FIG. 4 shows schematically a method of manufacturing an absorbent product, including the steps of
- cutting 130 a plurality of slits 2 in a central region 4 of a continuous web of liquid inlet foam material 101, said slits extending longitudinally in the machine direction;
- extending 131 the web of liquid inlet foam material 101 transversally in the cross machine direction, whereby the slits 2 are dilated into openings 3;
- applying adhesive 132 to a continuous web of carrier material 110;
- combining 133 the continuous web of liquid inlet foam material 101 and the web of carrier material 110 into a combined web 125;
- cutting 134 inlet foam layer components 126 from the combined web 125;
- providing 135 discrete absorbent components 122;
- enclosing 136 the inlet foam layer component 126 and absorbent component 122 between a continuous web of topsheet material 107 and a continuous web of backsheet material 108;
- joining 137 at least the topsheet material 107 and the backsheet material 108 along the outer edges of the absorbent product; and
- cutting 138 the combined material into a desired shape, thus obtaining the absorbent product 100.

When extending 131 the web of liquid inlet foam material 101 transversally in the cross machine direction, the width of said web of liquid inlet foam material 101 is extended to a predetermined desired transversal width M4, and when applying adhesive 132 to the continuous web of carrier material 110, the adhesive is applied intermittently, so that adhesive is applied on sections 116 of the web of carrier material 110, which correspond to the intermediate portion 16 of the absorbent core 11, and sections 117, which correspond to the front and rear end portions 15, 17 of the absorbent core 11 are free from adhesive.

Alternatively, when extending 131 the web of liquid inlet foam material 101 transversally in the cross machine direction, the width of said web of liquid inlet foam material 101 is extended intermittently, so that sections 216 of the web of liquid inlet foam material 101 is extended to a predetermined desired transversal width M4, and sections 117, which correspond to the front and rear end portions 15, 17 of the absorbent core 11 retain their original unextended width, and when applying adhesive 132 to the continuous web of carrier material 110, the adhesive is applied continuously to the web of carrier material 110.

The method shown in FIG. 4 also includes applying adhesive 139 to the surface of the web of topsheet material 107 facing the liquid inlet foam component 126 before enclosing the core components 126, 122, and pressing the layers together 135 so that the topsheet material layer 107 attaches to the carrier layer 110 through the openings 3 formed in the liquid inlet foam layer 101.

Examples

The thickness of a foam layer suitable for the liquid inlet layer is measured with an applied pressure of 0.5 kPa on a non-apertured and non-stretched piece of material. The thickness gauge foot suitably measures 45×45 mm, or in any way it must be smaller than the foam sample. Carefully separate the foam from the article, and measure thickness on a representative area. Lower the foot slowly and gently over the sample, and let it rest for 10 seconds before reading the thickness. In case the foam has an irregular thickness, an average value should be taken from five representative measurement spots.

Density is calculated by weighing the sample (in grams), and then dividing the weight by the sample volume (in $cm^3$). Volume is measured by multiplying the thickness (measured as above) by the sample area. The foam density refers to homogenous foam material, thus excluding any slits or openings.

Opacity is measured according to International Standard ISO 2471:2008(E)—Paper and board—Determination of opacity (paper backing)—Diffuse reflectance method. The method originates from the paper industry, but it is suitable also in this context. Carefully separate the inlet layer from the absorbent product. Measure opacity on an area that is free from slits or apertures. In case the opacity varies over the area of the inlet layer, e.g. due to partial coloration or differences in basis weight, the least opaque area should be considered representative for the inlet layer.

Table 1 below shows examples of suitable commercially available foam materials that can be used for the liquid inlet layer of the absorbent core.

TABLE 1

Measurements on foam materials

| | Material designation | Material type | Thickness (mm) | Basis Weight (g/m$^2$) | Density (kg/m$^3$) | Opacity, (%) ISO 2471* |
|---|---|---|---|---|---|---|
| 1 | Recticel Bulfast 35H | Polyurethane foam | 1.96 | 66.9 | 34.1 | 35 |
| 2 | Recticel T23/20 | polyurethane foam | 2.54 | 55.0 | 21.7 | 32 |
| 3 | Recticel T25090 | polyurethane foam | 2.37 | 55.2 | 23.3 | 34 |
| 4 | Recticel T46090 | polyurethane foam | 3.11 | 126.5 | 40.7 | 42 |
| 5 | FXI CAZ080A | polyurethane foam | 1.81 | 57.9 | 32.0 | 53 |

*ISO 2471: 2008 (E) - Paper and board - Determination of opacity (paper backing) - Diffuse reflectance method A liquid inlet foam material having low thickness and density can be preferred for reasons of comfort and discretion.

The material of sample 5 is a foam having high reflection due to inclusion of white pigment. The foam of sample 4 has relatively high thickness and basis weight, which gives a higher opacity. The material of sample 2 is a foam having the most preferred opacity, although all foams in the table are transparent enough to be suitable for the liquid inlet layer.

The invention claimed is:

1. An absorbent product comprising:
a liquid permeable topsheet;
a liquid impermeable backsheet; and
an absorbent core enclosed between the topsheet and the backsheet, said absorbent core having a length extending in a longitudinal direction of the absorbent product, between a front edge and a rear edge; longitudinally extending side edges; a front end portion; a rear end portion; and an intermediate portion located between the front and rear portions in the longitudinal direction of the absorbent core, and said absorbent core comprising:
an absorbent fibrous layer arranged on a side of the absorbent core closest to the liquid impermeable backsheet,
a liquid inlet foam layer arranged on a side of the absorbent core closest to the liquid permeable topsheet, and
a carrier layer arranged between the liquid inlet foam layer and the absorbent fibrous layer,
wherein the liquid inlet foam layer includes a transversally central region extending along the entire longitudinal length of the absorbent core and having longitudinally extending side edges,
wherein the liquid inlet foam layer comprises a plurality of slits arranged in a pattern, which covers the transversally central region such that, in a part of said transversally central region within the intermediate portion of the absorbent core, the slits are in the form of dilated slit openings, and, in a part of said transversally central region within one or both of the front end portion and rear end portion of the absorbent core, the slits are in the form of non-dilated slits.

2. The absorbent product of claim 1, wherein the dilated slit openings are formed from a plurality of slits that have been dilated into dilated slit openings by transversally stretching a web of liquid inlet foam material, from which the liquid inlet foam layer is made, before incorporation into the product.

3. The absorbent product of claim 1, wherein the non-dilated slits have a maximum transversal opening width of 0-1 mm, and the dilated slit openings have a maximum transversal opening width of 1.5-15 mm.

4. The absorbent product of claim 1, wherein one or both of said front end portion and rear end portion comprise non-dilated slits, but no dilated slit openings.

5. The absorbent product of claim 1, further comprising at least one of:
a front transition region located between the front end portion and the intermediate portion in the longitudinal direction of the absorbent core, and
a rear transition region located between the rear end portion and the intermediate portion in the longitudinal direction of the absorbent core,
wherein, in one or both said front transition region and said rear transition region, an amount of dilation of the slits gradually increases from non-dilated slits to dilated slit openings in a direction from said front transition region or said rear transition region toward the intermediate portion.

6. The absorbent product of claim 1, wherein said front end portion and said rear end portion each have a length in the longitudinal direction from the front end edge and the rear end edge, respectively, of 5 mm.

7. The absorbent product of claim 1, wherein the carrier layer s made of a material having a different color than material from which the liquid inlet foam layer is made.

8. The absorbent product of claim 1, wherein colored areas are present on the carrier layer in the front end portion and rear end portion of the absorbent core.

9. The absorbent product of claim 8, wherein material from which the liquid inlet foam layer is made has an opacity of 20-100%.

10. The absorbent product of claim 8, wherein the liquid permeable topsheet comprises a see-through material, through which is visible either the colored areas or difference in color of material from which the carrier layer is made in relation to material form which the liquid inlet foam layer is made.

11. The absorbent product of claim 1, wherein the liquid inlet foam layer further comprises side edge regions located on either side of the central region in the transversal direction of the absorbent product, between the central region and the longitudinal side edges of the absorbent core, and wherein the liquid inlet foam layer in each of said side edge regions is free from slits.

12. The absorbent product of claim 1, wherein the central region has a transversal width and the absorbent fibrous layer has a minimum width, and wherein the transversal width of the central region is equal to or smaller than the minimum width of the absorbent fibrous layer.

13. A method of manufacturing an absorbent product, comprising:
cutting a plurality of slits in a central region of a continuous web of liquid inlet foam material, said slits extending longitudinally in the machine direction;
stretching the web of liquid inlet foam material transversally in the cross machine direction such that the slits are dilated into dilated slit openings;
applying adhesive to a continuous web of carrier material;
combining the stretched continuous web of liquid inlet foam material and the web of carrier material into a combined web;

cutting an inlet foam layer component from the combined web;

providing an absorbent component;

enclosing the inlet foam layer component and the absorbent component between a continuous web of topsheet material and a continuous web of backsheet material;

joining at least the topsheet material and the backsheet material along the outer edges of the absorbent product to form a combined material;

cutting the combined material into a desired shape to form the absorbent product, wherein the stretching of the web of liquid inlet foam material and the applying adhesive to the continuous web of carrier material is performed according to one of the following:

when stretching the web of liquid inlet foam material transversally in the cross machine direction, the width of said web of liquid inlet foam material is stretched to a predetermined desired transversal width, and when applying adhesive to the continuous web of carrier material, the adhesive is applied intermittently, so that adhesive is applied on sections of the web of carrier material, which correspond to an intermediate portion of the absorbent core, and sections, which correspond to a front end portion and a rear end portion of the absorbent core, are free from adhesive;

or when stretching the web of liquid inlet foam material transversally in the cross machine direction, the width of said web of liquid inlet foam material is stretched intermittently, so that sections of the web of liquid inlet foam material is stretched to a predetermined desired transversal width, and sections, which correspond to the front end portion and the rear end portion of the absorbent core, retain their original unstretched width, and when applying adhesive to the continuous web of carrier material, the adhesive is applied continuously to the web of carrier material.

14. The method of claim 13, wherein the slits have a length in the longitudinal direction of 3.0-20.0 mm.

15. The method of claim 13, further comprising applying adhesive to the surface of the web of topsheet material facing the inlet foam layer component before enclosing the inlet foam layer component and the absorbent component within the topsheet material and the backsheet material, and then during the step of joining the topsheet material and the backsheet material to form the combined material, the topsheet material is pressed against the inlet foam layer component such that the topsheet material is attached to the carrier layer through the dilated slit openings formed in the liquid inlet foam material.

16. The method of claim 13, wherein the web of carrier material has a different color than the web of liquid inlet foam material.

17. The method of claim 13, wherein the web of carrier material comprises one or more colored areas applied thereto.

18. The method of claim 17, wherein the one or more colored areas are printed on a body facing surface or on a garment facing surface of the web of carrier material.

* * * * *